United States Patent
Hirson et al.

(10) Patent No.: US 9,765,270 B2
(45) Date of Patent: *Sep. 19, 2017

(54) FUEL GENERATION USING HIGH-VOLTAGE ELECTRIC FIELDS METHODS

(71) Applicant: POWERDYNE, INC., Newport Beach, CA (US)

(72) Inventors: Geoffrey Hirson, Newport Beach, CA (US); Gus F. Shouse, Newport Beach, CA (US)

(73) Assignee: POWERDYNE, INC., Newport Beach, CA (US)

( * ) Notice: Subject to any disclaimer, the term of this patent is extended or adjusted under 35 U.S.C. 154(b) by 183 days.

This patent is subject to a terminal disclaimer.

(21) Appl. No.: 14/426,248

(22) PCT Filed: Sep. 5, 2013

(86) PCT No.: PCT/US2013/058315
§ 371 (c)(1),
(2) Date: Mar. 5, 2015

(87) PCT Pub. No.: WO2014/039711
PCT Pub. Date: Mar. 13, 2014

(65) Prior Publication Data
US 2015/0232772 A1 Aug. 20, 2015

Related U.S. Application Data

(60) Provisional application No. 61/697,148, filed on Sep. 5, 2012.

(51) Int. Cl.
*C10L 1/04* (2006.01)
*C10G 2/00* (2006.01)
*C01B 3/12* (2006.01)

(52) U.S. Cl.
CPC .... *C10L 1/04* (2013.01); *C01B 3/12* (2013.01); *C10G 2/332* (2013.01); *C10G 2/333* (2013.01);
(Continued)

(58) Field of Classification Search
CPC ............... C10L 1/04; C10L 2200/0492; C10L 2270/023; C10L 2270/026; C10L 2270/04;
(Continued)

(56) References Cited

U.S. PATENT DOCUMENTS 1,746,464 A 2/1930 Fischer et al.
3,979,205 A 9/1976 Wanzenberg
(Continued)

FOREIGN PATENT DOCUMENTS

CA 2379892 A1 2/2001
CN 1268550 A 10/2000
(Continued)

OTHER PUBLICATIONS

Supplemental European Search Report for EP13836174 dated Mar. 31, 2016.
(Continued)

*Primary Examiner* — Xiuyu Tai
(74) *Attorney, Agent, or Firm* — Pepper Hamilton LLP

(57) ABSTRACT

Methods of making fuel are described herein. A method may include providing a first working fluid, a second working fluid, and a third working fluid. The method may also include exposing the first working fluid to a first high voltage electric field to produce a first plasma, exposing the second working fluid to a second high voltage electric field to produce a second plasma, and exposing the third working fluid to a third high voltage electric field to produce a third plasma. The method may also include providing and con-
(Continued)

tacting a carbon-based feedstock with the third plasma, the second plasma, and the first plasma within a processing chamber to form a mixture, cooling the mixture using a heat exchange device to form a cooled mixture, and contacting the cooled mixture with a catalyst to form a fuel.

25 Claims, 5 Drawing Sheets

(52) U.S. Cl.
CPC ........ *C10G 2/50* (2013.01); *C01B 2203/0283* (2013.01); *C01B 2203/062* (2013.01); *C01B 2203/0861* (2013.01); *C10L 2200/0492* (2013.01); *C10L 2270/023* (2013.01); *C10L 2270/026* (2013.01); *C10L 2270/04* (2013.01); *C10L 2290/06* (2013.01); *C10L 2290/30* (2013.01); *C10L 2290/42* (2013.01)

(58) Field of Classification Search
CPC ............. C10L 2290/38; C10L 2290/42; C10L 2290/06; C10G 2/332; C10G 2/50; C10G 2/333; C01B 2203/1205; C01B 3/12; C01B 2203/0283; C01B 2203/062; C01B 2203/0861; F01K 25/00; F01K 21/04; F22B 1/00; F22B 1/281; F23J 15/04; H02K 7/1823; C02F 1/006; C02F 1/30; C02F 1/302; C02F 1/305; C02F 1/34; C02F 1/4608; C02F 1/385; C02F 2301/024; C02F 2301/026; B04C 9/00; B04C 5/24; B04C 5/103; B04C 2009/007
See application file for complete search history.

(56) References Cited

U.S. PATENT DOCUMENTS

| | | |
|---|---|---|
| 4,466,807 A | 8/1984 | Santen et al. |
| 4,508,040 A | 4/1985 | Santen et al. |
| 4,591,428 A | 5/1986 | Pronk |
| 4,770,109 A | 9/1988 | Schlienger |
| 4,831,944 A | 5/1989 | Durand et al. |
| 4,845,334 A | 7/1989 | Stocks et al. |
| 4,898,748 A | 2/1990 | Kruger, Jr. |
| 5,046,144 A | 9/1991 | Jensen |
| 5,107,517 A | 4/1992 | Lauren |
| 5,136,137 A | 8/1992 | Schlienger |
| 5,138,959 A | 8/1992 | Kulkarni |
| 5,288,969 A | 2/1994 | Wong et al. |
| 5,301,620 A | 4/1994 | Nagel et al. |
| 5,319,176 A | 6/1994 | Alvi et al. |
| 5,493,578 A | 2/1996 | Fukusaki et al. |
| 5,534,659 A | 7/1996 | Springer et al. |
| 5,541,386 A | 7/1996 | Alvi et al. |
| 5,544,597 A | 8/1996 | Camacho |
| 5,611,947 A | 3/1997 | Vavruska |
| 5,634,414 A | 6/1997 | Camacho |
| 5,666,891 A | 9/1997 | Titus et al. |
| 5,673,635 A | 10/1997 | Fowler |
| 5,725,616 A | 3/1998 | Lynum et al. |
| 5,798,496 A | 8/1998 | Eckhoff et al. |
| 5,868,027 A | 2/1999 | Norton et al. |
| 5,935,293 A | 8/1999 | Detering et al. |
| 5,958,264 A | 9/1999 | Tsantrizos et al. |
| 6,127,645 A | 10/2000 | Titus et al. |
| 6,153,852 A | 11/2000 | Blutke et al. |
| 6,173,002 B1 | 1/2001 | Robert |
| 6,187,226 B1 | 2/2001 | Detering et al. |
| 6,215,678 B1 | 4/2001 | Titus et al. |
| 6,289,851 B1 | 9/2001 | Rabovitser et al. |
| 6,355,904 B1 | 3/2002 | Batdorf et al. |
| 6,372,156 B1 | 4/2002 | Kong et al. |
| 6,375,832 B1 | 4/2002 | Eliasson et al. |
| 6,505,567 B1 | 1/2003 | Liljedahl et al. |
| 6,524,538 B2 | 2/2003 | Barankova et al. |
| 6,552,295 B2 | 4/2003 | Markunas et al. |
| 6,810,821 B2 | 11/2004 | Chan |
| 6,821,500 B2 | 11/2004 | Fincke et al. |
| 6,874,434 B1 | 4/2005 | Bigelow et al. |
| 6,971,323 B2 | 12/2005 | Capote et al. |
| 6,976,362 B2 | 12/2005 | Sheppard et al. |
| 6,987,792 B2 | 1/2006 | Do et al. |
| 7,070,634 B1 | 7/2006 | Wang |
| 7,097,675 B2 | 8/2006 | Detering et al. |
| 7,279,655 B2 | 10/2007 | Blutke et al. |
| 7,335,320 B2 | 2/2008 | Kingdig et al. |
| 7,384,619 B2 | 6/2008 | Bar-Gadda |
| 7,576,296 B2 | 8/2009 | Fincke et al. |
| 7,622,693 B2 | 11/2009 | Foret |
| 7,674,443 B1 | 3/2010 | Davis |
| 7,832,344 B2 | 11/2010 | Capote et al. |
| 7,845,411 B2 | 12/2010 | Vinegar et al. |
| 7,981,371 B2 | 7/2011 | Meillot et al. |
| 8,129,654 B2 | 3/2012 | Lee et al. |
| 8,168,128 B2 | 5/2012 | Seeley et al. |
| 8,199,790 B2 | 6/2012 | Vera |
| 8,216,433 B2 | 7/2012 | Yonesu |
| 8,252,244 B2 | 8/2012 | Capote et al. |
| 8,268,094 B2 | 9/2012 | Zurecki et al. |
| 8,277,631 B2 | 10/2012 | Eastman et al. |
| 8,303,916 B2 | 11/2012 | Collins et al. |
| 8,324,523 B2 | 12/2012 | Foret |
| 8,357,837 B2 | 1/2013 | Pleines et al. |
| 8,367,005 B2 | 2/2013 | Ikeda et al. |
| 8,475,551 B2 | 7/2013 | Tsangaris et al. |
| 8,518,162 B2 | 8/2013 | Smith et al. |
| 8,519,354 B2 | 8/2013 | Charipar et al. |
| 2002/0000085 A1 | 1/2002 | Hall et al. |
| 2002/0040889 A1 | 4/2002 | Markunas et al. |
| 2002/0151604 A1 | 10/2002 | Detering et al. |
| 2003/0029796 A1 | 2/2003 | Maekawa |
| 2003/0065042 A1 | 4/2003 | Shaw |
| 2003/0209174 A1 | 11/2003 | Chan |
| 2004/0134517 A1 | 7/2004 | Clark |
| 2004/0251241 A1 | 12/2004 | Blutke et al. |
| 2006/0053791 A1 | 3/2006 | Prentice, III |
| 2006/0060464 A1 | 3/2006 | Chang |
| 2006/0112639 A1 | 6/2006 | Nick et al. |
| 2006/0201157 A1 | 9/2006 | Villalobos |
| 2006/0233699 A1 | 10/2006 | Mills |
| 2007/0017228 A1 | 1/2007 | Surma |
| 2007/0186474 A1 | 8/2007 | Rabovitser et al. |
| 2007/0253874 A1 | 11/2007 | Foret |
| 2007/0258869 A1 | 11/2007 | Tsangaris et al. |
| 2007/0266633 A1 | 11/2007 | Tsangaris et al. |
| 2007/0267289 A1 | 11/2007 | Jabs et al. |
| 2007/0272131 A1 | 11/2007 | Carabin et al. |
| 2008/0041829 A1 | 2/2008 | Blutke et al. |
| 2008/0083701 A1 | 4/2008 | Shao et al. |
| 2008/0147241 A1 | 6/2008 | Tsangaris et al. |
| 2008/0184621 A1 | 8/2008 | Clark |
| 2008/0202028 A1 | 8/2008 | Tsangaris et al. |
| 2008/0209807 A1 | 9/2008 | Tsangaris et al. |
| 2008/0222956 A1 | 9/2008 | Tsangaris et al. |
| 2008/0223047 A1 | 9/2008 | Oliver |
| 2008/0277265 A1 | 11/2008 | Tsangaris et al. |
| 2008/0283153 A1 | 11/2008 | Zurecki et al. |
| 2008/0283411 A1 | 11/2008 | Eastman et al. |
| 2008/0290322 A1 | 11/2008 | Hederer et al. |
| 2009/0038958 A1 | 2/2009 | Coyle et al. |
| 2009/0049748 A1* | 2/2009 | Day ........................ C01B 3/342 48/77 |
| 2009/0133407 A1 | 5/2009 | Sawyer |
| 2009/0183430 A1 | 7/2009 | Schubert et al. |
| 2009/0188127 A1 | 7/2009 | Gorbell et al. |
| 2009/0307975 A1 | 12/2009 | Wolf |
| 2010/0050654 A1 | 3/2010 | Chiu et al. |
| 2010/0065781 A1 | 3/2010 | Brothier |
| 2010/0167139 A1 | 7/2010 | Gattis et al. |
| 2010/0229522 A1 | 9/2010 | Kingzett |
| 2010/0298449 A1 | 11/2010 | Rojey |
| 2011/0067376 A1 | 3/2011 | Tompkins et al. |

(56) References Cited

U.S. PATENT DOCUMENTS

| | | | |
|---|---|---|---|
| 2011/0162523 A1 | 7/2011 | Fabbri et al. |
| 2011/0162958 A1 | 7/2011 | Cho et al. |
| 2011/0201700 A1 | 8/2011 | Lucas et al. |
| 2011/0212012 A1 | 9/2011 | McAlister |
| 2011/0265698 A1 | 11/2011 | Hirson et al. |
| 2011/0286893 A1 | 11/2011 | Zimmerman et al. |
| 2012/0000115 A1 | 1/2012 | Shastri |
| 2012/0032452 A1 | 2/2012 | Kuku |
| 2012/0070347 A1 | 3/2012 | Bacon et al. |
| 2012/0090985 A1 | 4/2012 | Rabinovich et al. |
| 2012/0114877 A1 | 5/2012 | Lee |
| 2012/0121468 A1 | 5/2012 | Tsangaris et al. |
| 2012/0291436 A1 | 11/2012 | Hirson et al. |
| 2013/0200624 A1 | 8/2013 | Hirson et al. |
| 2013/0300121 A1 | 11/2013 | Ali et al. |

FOREIGN PATENT DOCUMENTS

| | | |
|---|---|---|
| CN | 1810938 A | 8/2006 |
| EP | 1270508 A1 | 1/2003 |
| GB | 573982 | 12/1945 |
| WO | WO 2005/005009 A2 | 1/2005 |
| WO | WO 2008/130260 A1 | 10/2008 |
| WO | WO 2009/156761 A2 | 12/2009 |
| WO | WO 2010/056462 A1 | 5/2010 |
| WO | WO 2011/091327 A1 | 7/2011 |
| WO | WO 2011/140080 A2 | 11/2011 |
| WO | WO 2012/039751 A2 | 3/2012 |
| WO | WO 2012/064936 A1 | 5/2012 |
| WO | WO 2012/077198 A1 | 6/2012 |
| WO | WO 2012/158797 A1 | 11/2012 |
| WO | WO 2012/177666 A1 | 12/2012 |

OTHER PUBLICATIONS

Supplemental European Search Report for EP 13835933 dated Mar. 31, 2016.
Supplemental European Search Report for EP 13834468 dated Mar. 31, 2016.
Supplemental European Search Report for EP 13834969 dated Apr. 1, 2016.
Supplemental European Search Report for EP 13835425 dated Apr. 1, 2016.
Supplemental European Search Report for EP 13835534 dated Apr. 11, 2016.
Supplemental European Search Report for EP 13835723 dated Mar. 31, 2016.
International Search Report and Written Opinion dated Feb. 24, 2015 for International Application No. PCT/US2014/069342.
"C-17 flight uses synthetic fuel blend," (Oct. 25, 2007), Wright-Patterson Air Force Base, Retrieved Feb. 7, 2008, http://www.wpafb.af.mil/news/story.asp?id=123073170.
Fairley, Peter, "Growing Biofuels," (Nov. 23, 2005), MIT Technology Review, http://www.technologyreview.com/news/404941/growing-biofuels/.
"Governor Rendell leads with innovative solution to help address PA energy needs," State of Pennsylvania. Archived from original on Dec. 11, 2008, http://web.archive.org/web/20081211180710/http://www.state.pa.us/papower/cwp/view.asp?Q=446127&A=11.
Jamieson et al., "Keeping the Options Open", *Petroleum Economist*, Retrieved LNG 2012.
Krauss, Clifford, "South African Company to Build U.S. Plant to Convert Gas to Liquid Fuels," (Dec. 3, 2012), *New York Times*, http://www.nytimes.com/2012/12/04/business/energy-environment/sasol-plans-first-gas-to-liquids-plant-in-us.html? r=1.
Lane, Jim, "Little Big Tech: Can Fischer-Tropsch technology work at smaller scale?" *Biofuels Digest*, http://www.biofuelsdigest.com/bidigest/2012/11/20/little-big-tech-can-fisher-tropsch-technology-work-at-smaller-scale/.
"PetroSA Wins Innovation Award," SouthAfrica.info, (Oct. 10, 2008), Retrieved Dec. 18, 2012, http://www.southafrica.info/business/trends/innovations/petrosa-101008.htm.
"PetroSA technology ready for next stage," Businessday.co.za, (May 10, 2011) Retrieved Jun. 5, 2013, http://www.bdlive.co.za/articles/2011/05/10/petrosa-technology-ready-for-next-stage.
Pitt, Anthea, "Linc gears up for Chinchilla GTL," (Nov. 28, 2012), Upstreamonline.com, http://www.upstreamonline.com/live/article1149671.ece?print=preview.
"Schweitzer wants to convert Otter Creek coal into liquid fuel," (Aug. 2, 2005), *Billings Gazette*, Archived from original on Jan. 1, 2009.
Smedley, Mark, "Small GTL's Market Reach as Great as Opec's, UK Firm Says," *World Gas Intelligence*, Retrieved Dec. 19, 2012, http://www.oxfordcatalysts.com/press/egs/world_gas_intelligence_121219.pdf.
Steynberg et al., "Clean Coal Conversion Options Using Fischer-Tropsch Technology," (2003), Fuel Chemistry Division Preprints, 48(1); 459-461.
"UPM-Kymmene says to establish beachhead in biodesel market," NewsRoom Finland. Archived from original on Mar. 17, 2007, http://web.archive.org/web/20070317104947/http:/newsroom.finland.fi/stt/showarticle.asp?intNWSAID=14179&group=Business.
International Search Report and Written Opinion dated Jul. 28, 2014 for International Application No. PCT/US2014/024606.
International Search Report and Written Opinion dated Jan. 17, 2014 for International Application No. PCT/US2013/058287.
International Search Report and Written Opinion dated Feb. 7, 2014 for International Application No. PCT/US2013/058301.
International Search Report and Written Opinion dated Dec. 12, 2013 for International Application No. PCT/US2013/058305.
International Search Report and Written Opinion dated Feb. 7, 2014 for International Application No. PCT/US2013/058315.
International Search Report and Written Opinion dated Feb. 7, 2014 for International Application No. PCT/US2013/058326.
International Search Report and Written Opinion dated Jan. 22, 2014 for International Application No. PCT/US2013/058331.
International Search Report and Written Opinion dated Jan. 16, 2014 for International Application No. PCT/US2013/058335.
Plasco Group, "How is Plasco Different?," http://www.plascoenergygroup.com/our-solution/how-is-plasco-different/, retrieved from web Jul. 5, 2011.
Schuey et al., "LLW Processing and Operational Experience Using a Plasma ARC Centrifugal Treatment (PACT) System," *WM'06 Conference*, Feb. 26-Mar. 2, 2006, Tucson, AZ.
Urashima et al., "Removal of Volatile Organic Compounds from Air Streams and Industrial Flue Gases by Non-Thermal Plasma Technology," *IEEE Transactions on Dielectrics and Electrical Insulation*, Oct. 2000, 7(5):602-614.

\* cited by examiner

FUEL GENERATION USING HIGH-VOLTAGE ELECTRIC FIELDS METHODS

CLAIM OF PRIORITY

This application is a national phase application under 35 U.S.C. §371 of International Application No. PCT/US2013/058315, entitled "Fuel Generation Using High-Voltage Electric Fields Methods," and filed Sep. 5, 2013, which claims the benefit of and priority to U.S. Provisional Patent Application No. 61/697,148, entitled "Methods for Generating Fuel Materials and Power, and Sequestering Toxins Using Plasma Sources," which was filed on Sep. 5, 2012. The aforementioned applications are incorporated by reference herein in their entireties and for all purposes.

BACKGROUND

Fuel materials come in a wide variety of forms, from simple gases such as hydrogen to complex mixtures typically found in aviation fuels. Due to the wide range of chemical compositions for each type of fuel, fuels may be generated through a variety of processes. As a result, certain fuels may require dedicated facilities for fuel synthesis. Accordingly, such facilities may be optimized to generate only the fuels to which they are dedicated. In addition, each facility may require feedstocks and/or precursor materials for fuel synthesis.

Developing high efficiency methods for generating a variety of gaseous and/or liquid fuels from a limited number of readily available feed stocks is of high interest. Improved efficiency may be obtained in part by having the fuel generating facility also produce at least some electric power to lessen the facility's dependence on external power sources. Improved efficiency may also be obtained by a facility having multiple points of process control to properly adjust reaction temperatures and various other process conditions to optimize the fuel generation methods.

SUMMARY

In an embodiment, a method of making fuel may include providing a first working fluid, a second working fluid, and a third working fluid. The method may also include exposing the first working fluid to a first high voltage electric field to produce a first plasma, exposing the second working fluid to a second high voltage electric field to produce a second plasma, and exposing the third working fluid to a third high voltage electric field to produce a third plasma. The method may also include providing and contacting a carbon-based feedstock with the third plasma, the second plasma, and the first plasma within a processing chamber to form a mixture, cooling the mixture using a heat exchange device to form a cooled mixture, and contacting the cooled mixture with a catalyst to form a fuel.

DETAILED DESCRIPTION

Figure 1A:
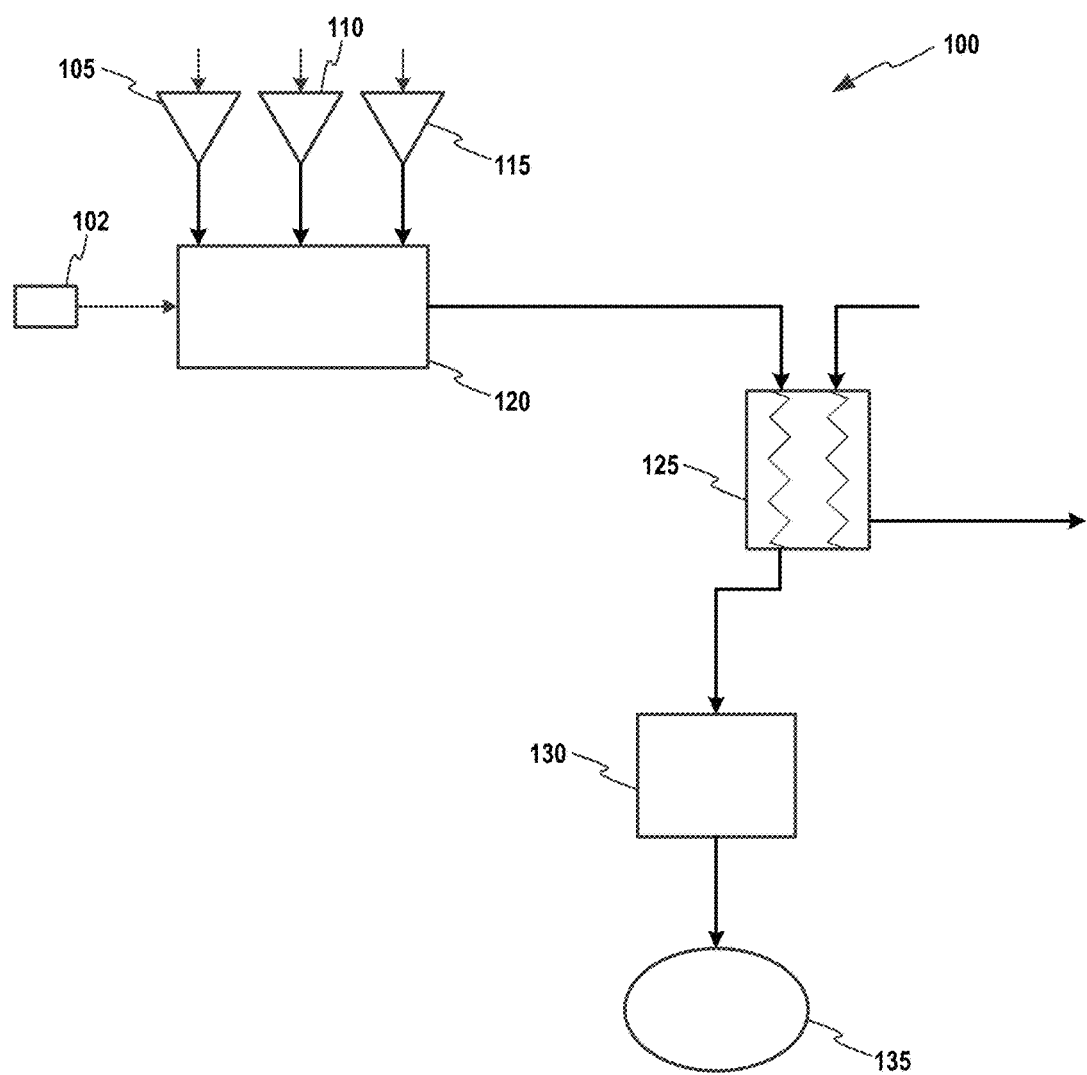
FIG. 1A depicts a block diagram of a system for generating fuel from at least one plasma source according to an embodiment.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The following terms shall have, for the purposes of this application, the respective meanings set forth below.

As used herein, a fuel refers to any composition of matter that provides a source of energy. Particular fuels that may be used herein include naphtha, diesel fuel, a diesel fuel blend, Jet Propellant 8 (JP-8) fuel, jet fuel, a jet fuel blend, or gasoline. Naphtha may be a process stream that contains predominantly five carbons and heavier chemical components. Naphtha may include a debutanized stream of cracked hydrocarbons that may be processed and used, for example, as a gasoline blending stock. Jet fuel may be a fuel that is generally suitable for use as an aviation fuel. Jet fuel may comply with one or more regulations or requirements, such as, for example, ASTM D 1655 Specification for Aviation Turbine Fuels. In some embodiments, the jet fuel may be a liquid hydrocarbon fuel. In some embodiments, the jet fuel may include paraffins as a major component, as well as various aromatics and napthenes. A blend, such as the diesel fuel blend or the jet fuel blend, refers to a fuel blend that contains at least in part diesel fuel or jet fuel, respectively.

A plasma torch refers to any device capable of generating a directed flow of plasma. Illustrative plasma torches may include, but are not limited to, ionized gas plasma generating systems, such as Inductively Coupled Plasma, Transferred Arc DC Plasma, and Non-Transferred Arc DC Plasma. As used herein, the terms "torch" or "torches" refer to plasma torches. Plasma torches may be capable of reaching temperatures ranging of up to about 10,000° F. to about 20,000° F. (about 5,540° C. to about 11,080° C.), or more. Each plasma torch may be a portion of a plasma reactor, which is generally a combination of a plasma torch and a reaction vessel with which the plasma torch is used.

A Fischer-Tropsch process as used herein refers to a series of chemical reactions that produce a variety of hydrocarbon molecules according to the formula ($C_nH_{(2n+2)}$). The series of chemical reactions may produce alkanes as follows:

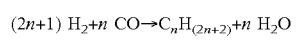

$(2n+1) H_2 + n\ CO \rightarrow C_nH_{(2n+2)} + n\ H_2O$ where n is a positive integer. The formation of methane (n=1) may generally be excluded as methane is gaseous at standard temperature and pressure. Most of the alkanes produced tend to be straight-chain and may be suitable as fuel. In addition to alkane formation, competing reactions give small amounts of alkenes, as well as alcohols and other oxygenated hydrocarbons, as described in greater detail herein.

In various embodiments described herein, a method of making fuel may include exposing a first working fluid to a first high-voltage electric field to produce a first plasma, exposing a second working fluid to a second high-voltage electric field to produce a second plasma, exposing a third working fluid to a third high-voltage electric field to produce a third plasma, and contacting the first plasma, the second fluid plasma, and the third plasma with a feedstock to form a mixture. The mixture may be transported to a heat exchange device that may cool the mixture to form a cooled mixture. The cooled mixture may be contacted with a catalyst to form a fuel. In some non-limiting examples, the fuel may include at least one of naphtha, diesel fuel, a diesel fuel blend, JP-8 fuel, jet fuel, or a jet fuel blend. In some embodiments, a particular amount of the various ingredients (feedstock, working fluids) may result in a particular amount of fuel produced. For example, about 30 tons of feedstock may be used to produce about 500 gallons to about 750 gallons of fuel.

FIG. 1A depicts a system for making fuel according to an embodiment. The system, generally designated 100, may include a feedstock source 102, one or more high-voltage electric field generators, such as 105, 110, 115, a first processing chamber (FPC) 120, a heat exchanger 125, a second processing chamber (SPC) 130, and a fuel storage tank 135.

The feedstock source 102 may generally include a feedstock material and may be configured to provide the feedstock material to the first processing chamber 120. In some embodiments, the feedstock may be a carbon-based feedstock. Such a carbon-based feedstock may be supplied from a carbon-based feedstock supply. Without limitation, illustrative examples of the feedstock may include one or more of bagasse, coal, wood, green waste, sugar beets, corn, or bio-waste products. Bagasse, as used herein, may generally refer to any fibrous matter obtained from a plant-based source. Thus, in one non-limiting example, bagasse may include fibrous matter obtained from sugarcane or sorghum stalks, particularly after the stalks have been crushed to remove their juice. Green waste may generally include biodegradable waste that can be comprised of garden or park waste material such as grass cuttings, flower cuttings, hedge trimmings, leaves, shrubs, plants, and tree trimmings, and/or waste from fruit and food processing. Bio-waste products may generally include kitchen waste, such as, for example, food scraps, which may be of animal or plant origin.

The mechanical components used by the feedstock source 102 to provide the feedstock to the FPC may be controlled according to various process parameters. The control of the transport of the feedstock may be supplied by a control system. In some embodiments, the control system may be specific to the mechanical components used to provide the feedstock to the FPC. In other embodiments, the control system may be incorporated into a control system to control the entire system 100, as described in greater detail herein.

Figure 1B:
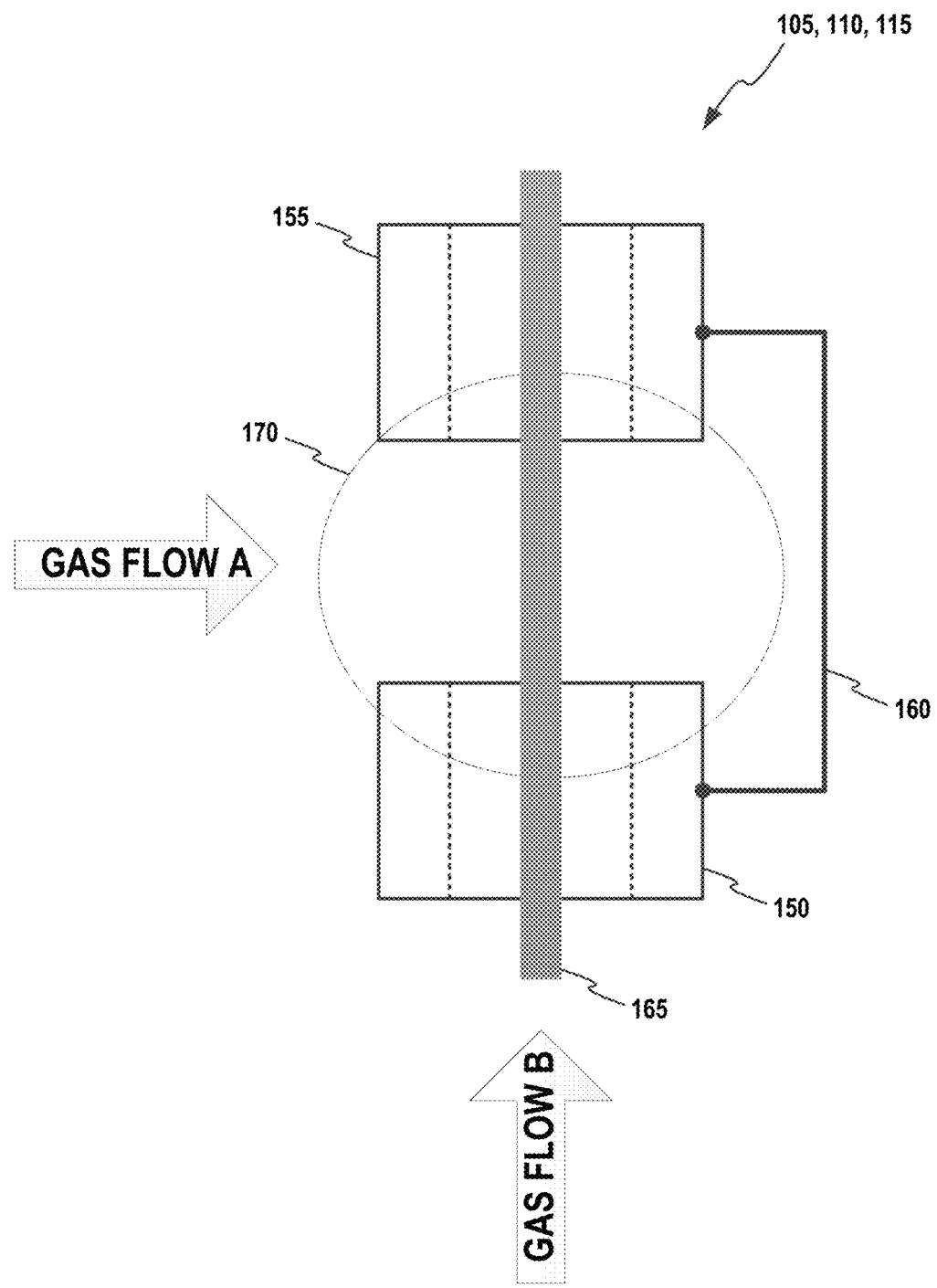
FIG. 1B depicts a block diagram of a high-voltage electric field generator according to an embodiment.

Each of the one or more high-voltage electric field generators 105, 110, 115 may generally be any of various components that may be used to generate a high voltage potential. Thus, as shown in FIG. 1B, each of the one or more high-voltage electric field generators 105, 110, 115 may have at least one anode surface 150, at least one cathode surface 155, and an electric potential 160 between the anode surface and the cathode surface. As a result, a magnetic field 165 and an electric field 170 may be generated when the electric potential 160 is applied between the at least one anode surface 150 and the at least one cathode surface 155. In some embodiments, a flow of gas, as described in greater detail herein and indicated by the horizontal arrow, may be substantially perpendicular to the magnetic field 165. In other embodiments, the flow of gas, as indicated by the vertical arrow, may be substantially parallel to the magnetic field 165. The magnetic field 165 and the electric field 170 may each have an effect on gas that flows through a gap between the anode surface 150 and the cathode surface 155. In a non-limiting example, the electric field 170 may stabilize the gas and/or ionize the gas. In another non-limiting example, the magnetic field 165 may alter a spin and/or a velocity of the gas.

Referring again to FIG. 1A, in some embodiments, each of the one or more high-voltage electric field generators 105, 110, 115 may be a plasma torch. While FIG. 1A depicts three high-voltage electric field generators 105, 110, 115, those skilled in the art will recognize that any number of high-voltage electric field generators may be used without departing from the scope of the present disclosure. Thus, for example, the system 100 may include 1, 2, 3, 4, 5, 6, 7, 8, or more high-voltage electric field generators.

It may be appreciated that a source of each of the one or more high-voltage electric field generators 105, 110, 115 may be controlled by one or more control systems (not shown). The one or more control systems may control all of the one or more high-voltage electric field generators 105, 110, 115 together and may be different from or included with a control system for the entire system 100. Alternatively, each of the one or more high-voltage electric field generators 105, 110, 115 may have a separate control system. A control system for a high-voltage electric field generator 105, 110, 115 may include control functions for torch parameters, such as the voltage of the plasma torch and a frequency of the plasma torch. Control of the high-voltage electric fields 105, 110, 115 may be based on one or more process measurements, including, but not limited to, a measurement of a voltage applied to components that generate the high-voltage electric field, a current drain of a voltage supply for high-voltage electric field generators, a temperature of the plasma output of the high-voltage electric field generators, and a composition of the plasma generated by the high-voltage electric field generators. It may further be appreciated that each of the high-voltage electric field generators (as illustrated by the high-voltage electric field generators 105, 110, 115) may be controlled according to one or more process algorithms. The high-voltage electric field generators 105, 110, 115 may be controlled according to the same process methods and/or algorithms (as provided by individual controllers or a single controller). Alternatively, each of the high-voltage electric field generators 105, 110, 115 may be controlled according to a different process method and/or algorithm (as provided by individual controllers or by a single controller).

The FPC 120 as used herein may generally refer to any chamber that is capable of withstanding one or more processing conditions such as temperature, pressure, corrosion, and the like under which the combustion of a working fluid in the presence of, for example, carbon dioxide, oxygen, and/or water takes place. In some embodiments, the FPC 120 may be incorporated with the one or more high-voltage electric field generators 105, 110, 115. In some embodiments, the FPC 120 may include one or more inlets for receiving plasma from the various high-voltage electric field generators 105, 110, 115 and feedstock from the feedstock source 102 and at least one outlet for discharging a mixture, as described in greater detail herein. An illustrative FPC 120 may be a plasma arc centrifugal treatment (PACT) system available from Retech Systems, LLC (Ukiah, Calif.), which includes at least one plasma torch.

In various embodiments, the FPC 120 may be maintained at a vacuum or near vacuum. In a particular embodiment, the FPC 120 may be maintained at a pressure of about 50 kPa to about 507 kPa (about 0.5 atmospheres to about 5 atmospheres), including about 50 kPa, about 100 kPa, about 150 kPa, about 200 kPa, about 250 kPa, about 300 kPa, about 350 kPa, about 400 kPa, about 450 kPa, about 500 kPa, about 507 kPa, or any value or range between any two of these values (including endpoints).

The mixture, while in the FPC 120, may attain temperatures of about 4000° C. to about 6000° C., as described in greater detail herein. Higher or lower temperatures may be attained according to various conditions under which the high-voltage electric field generators 105, 110, 115 operate. The mixture may be cooled within the FPC 120, at an exit port of the FPC, in a transport device (such as a pipe or other conduit) at an exit of the FPC, or at a combination of these locations using a coolant addition device (not shown). In some embodiments, the coolant addition device may use a coolant to effect cooling. An illustrative coolant may include liquid oxygen (LOX). An amount of coolant introduced into the mixture by the coolant addition device may be controlled by a control system. In some non-limiting examples, the amount of the coolant added to the mixture may be controlled according to a temperature of the mixture, a composition of the mixture, or other measured parameters of the mixture. In some embodiments, the control system may be associated only with the coolant addition device. In other embodiments, the control system may be incorporated into a system for controlling the entire system 100. The addition of the coolant to the mixture may reduce the temperature of the resulting mixture (an admixed mixture) to about 1450° C. to about 1650° C., including about 1450° C., about 1500° C., about 1550° C., about 1600° C., about 1650° C., or any value or range between any two of these values. It may be further appreciated that the admixed mixture may have a composition that is different from that of the mixture.

The heat exchanger 125 may generally be a device that is configured to transfer thermal energy from one medium to another such as, for example, a gas to another gas, a gas to a liquid, a liquid to another liquid, and the like. Illustrative examples of the heat exchanger 125 may include a steam generating heat exchanger (i.e., a boiler), a gas-gas interchanger, a boiler feed water exchanger, a forced air exchanger, a cooling water exchanger, or a combination thereof. Use of a plurality of heat exchangers 125, each producing successively lower pressure steam levels, is contemplated to be within the scope of the present disclosure. For example, the heat exchanger 125 may include a radiant heat exchanger, a convective heat exchanger, or a combination thereof. Steam and condensate may be generated from the heat exchange process and may include one or more steam products of different pressures. In a particular embodiment, the heat exchanger 125 may be a heat recovery steam generator (HRSG) such as, for example, a device manufactured by NEM (Leiden, Netherlands). The HRSG 125 may be configured so that no loss or degradation of the mixture occurs when the HRSG receives the mixture from the FPC 120. Thus, the HRSG 125 may be capable of withstanding various temperatures, pressures, corrosive chemicals, and the like when contacting the mixture. In some embodiments, the HRSG 125 may be lined with a ceramic to assist in accommodating an elevated temperature of the mixture. In some embodiments, the HRSG 125 may include a first inlet for receiving the mixture or the admixed mixture discharged from the FPC 120, a second inlet for receiving a fluid such as water, a first outlet for discharging steam, and a second outlet for discharging a cooled mixture, as described in greater detail herein. In some embodiments, an amount of water that enters the heat exchanger 125 via the second inlet may be controlled by a control system, as described in greater detail herein. A heated heat exchange material, which may include steam as a non-limiting example, may exit the heat exchanger 125 by means of the first outlet. The heated heat exchange material may be further transported to a first electric turbine to generate a first supply of electric power.

In various embodiments, the heat exchange material may be water, which may be converted to a supply of steam in the heat exchanger 125. Once the supply of steam has activated the electric turbine, the supply of steam may be cooled to liquid water. In some embodiments, the liquid water may be returned to the heat exchanger 125 to be reheated by more of the mixture or the admixed mixture. Alternatively, the first supply of steam, after activating the electric turbine, may be returned to a working fluid source to be supplied to one or more of the high-voltage electric field generators 105, 110, 115.

The second processing chamber 130 is not limited by this disclosure, and may generally be any type of structure, such as a chamber, a furnace, a tube, or the like, that may be used for controlling and containing a reaction. It will be appreciated that the second processing chamber may include a plurality of chambers. In particular embodiments, the second processing chamber 130 may be a chamber that is configured for any Fischer-Tropsch process.

The fuel storage tank 135 is not limited by this disclosure, and may generally be any vessel configured to at least receive fuel from the second processing chamber 130. In addition, the fuel storage tank 135 may, for example, be used to store fuel, transport fuel, dispense fuel, and/or the like.

In various embodiments, the system 100 may further include a gas separator (not shown). The gas separator may include, for example, a membrane separation system, a molecular sieve, or a combination thereof. The gas separator may generally be used to separate various components described herein, and may optionally deposit the separated components into various gas holding containers. The gas holding containers, for example, an $H_2$ container and a CO container, may each include an outflow metering device. Each outflow metering device may be controlled by a controller. Alternatively, the outflow metering devices of each of the gas holding containers may be controlled by the same controller. Each gas holding container may also have a gas output port associated with the outflow metering device. Each gas output port may direct the gas from the corresponding gas holding container into a common supply duct.

The outflow metering devices of each of the gas holding containers may be controlled to permit an amount of gas into the common supply duct to create a cooled mixture having a controlled composition, as described in greater detail herein. In one non-limiting example, the cooled mixture may be controlled based on one or more gas composition sensors associated with the common supply duct. In another non-limiting example, the cooled mixture may be controlled based on a volume of gas emitted by each outflow metering device. In yet another non-limiting example, the cooled mixture may be controlled based on the pressure of gas contained in each gas holding container. Accordingly, various ratios of the components of the cooled mixture, as described in greater detail herein, may be obtained.

Figure 2:
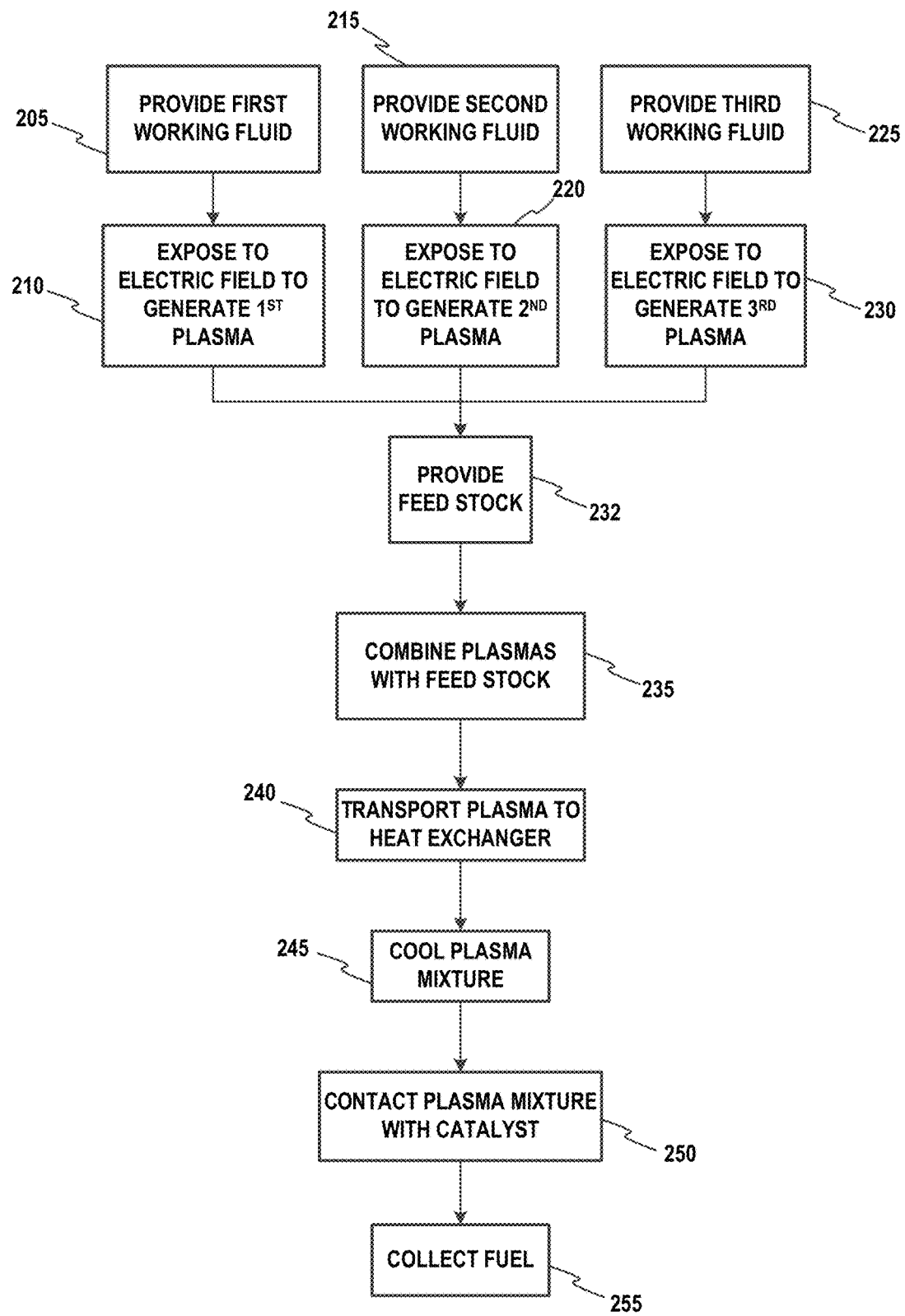
FIG. 2 depicts a flow diagram of a method of making fuel according to an embodiment.

FIG. 2 depicts a flow diagram of a method of making fuel according to an embodiment. The method may include providing 205 a first working fluid, providing 215 a second working fluid, and providing 225 a third working fluid. In one non-limiting embodiment, the first working fluid may be oxygen gas ($O_2$), the second working fluid may be water vapor ($H_2O$), and the third working fluid may be carbon dioxide gas ($CO_2$).

It may be appreciated that the $CO_2$, $O_2$, and $H_2O$ in the first processing chamber may be used as working fluids for the respective plasma torches, as described herein. Thus, each gas may be exposed to a high-voltage electric field. As a result of such exposure, the gases may be reduced to free radical species. For example, $H_2O$ may be reduced to a hydroxyl radical $OH^-$ and $O_2$ may be reduced to a superoxide anion radical $O_2^-$. In addition, the gases may be reduced to ionized species. For example, $O_2$ may be reduced to $O^-$, $O_2^-$, $O_2^+$, and/or $O^+$. The types and amounts of reactive species created by exposure of the gases to high-voltage electric fields may differ from those generated by exposure of the gases to heat alone.

Each working fluid may be supplied by its own working fluid source. In one non-limiting example, $CO_2$ may be supplied from a $CO_2$ source, $O_2$ may be supplied from an $O_2$ source, and water vapor ($H_2O$) may be supplied from an $H_2O$ source. It may be recognized that control of the fluid plasma from each of the high voltage field sources may also include control of the amount of working fluid supplied to each of the high voltage field sources. Although not shown, it is apparent that the working fluid supply sources for the $CO_2$, $O_2$, and $H_2O$ may also include control and measurement components. Such components may include, without limitation, components to control the amount of the working fluid supplied by each of the working fluid supply sources (valves) and devices to measure the amount of each of the working fluid supplied (such as, for example, by measuring chemical composition or pressure of the gas delivered). It may be further understood that such measurement and control devices may be controlled by one or more control systems, as disclosed above. In some embodiments, the control systems may be specific to one or more of the working fluid supply sources. In other embodiments, all working fluid supply sources may be controlled by the same control system. In some embodiments, the working fluid supply sources may be controlled by a control system common to the entire power generation system.

Although not illustrated herein, an embodiment may include three working fluids, such as $CO_2$, $O_2$, and $H_2O$, that may be combined into one or two combined working fluids before being supplied to one or more high-voltage electric field generators. As a non-limiting example, the $CO_2$, the $O_2$, and the $H_2O$ may be combined into a single combined working fluid to be supplied to a high-voltage electric field generator 105, 110, 115 (FIG. 1A). By extension, the controllers associated with each of the supply sources for the $CO_2$, the $O_2$, and the $H_2O$ may cause a specific amount of each gas to be added to the combined working fluid to produce an optimized ratio of gases. Similarly, the controller associated with a single plasma torch may cause the plasma torch to operate under optimum conditions for a specific ratio of gases in the combined working fluid.

Figure 3:
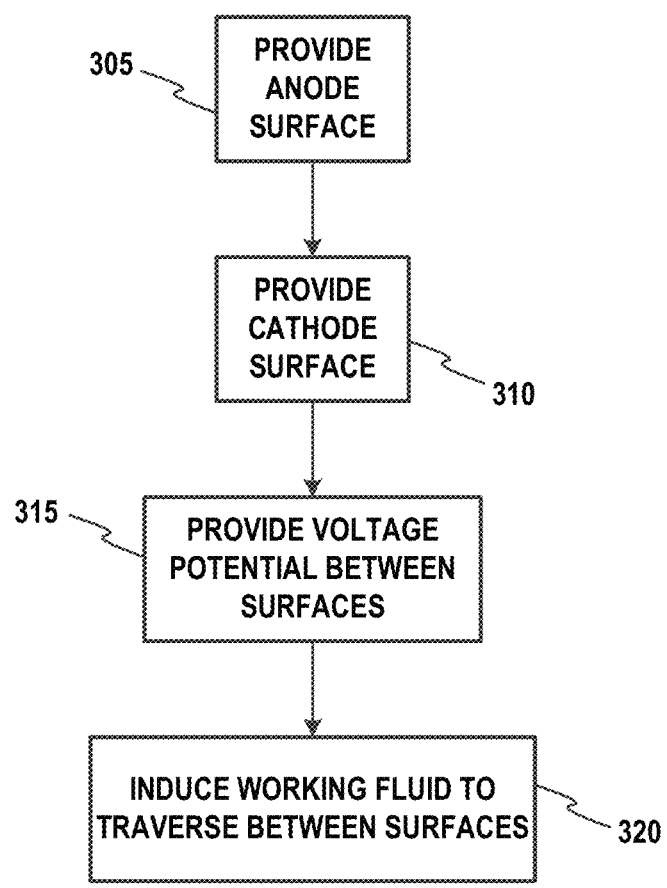
FIG. 3 depicts a flow diagram of a method of exposing a working fluid to a high voltage electric field according to an embodiment.

The first working fluid may be exposed 210 to a high-voltage electric field to generate a first plasma. As shown in FIG. 3, exposing 210 the first working fluid to the high-voltage electric field may include providing 305 an anode surface and providing 310 a cathode surface. The anode surface and the cathode surface may be separated by a distance to create a gap between the two surfaces. The distance may generally be selected such that (for the electrical voltage selected), the electrical field is about 0.3 kV/cm to about 8.0 kV/cm, including about 0.3 kV/cm, about 0.3149 kV/cm, about 0.5 kV/cm, about 0.75 kV/cm, about 1.0 kV/cm, about 1.25 kV/cm, about 1.5 kV/cm, about 1.574 kV/cm, about 2.0 kV/cm, about 2.5 kV/cm, about 3.0 kV/cm, about 3.149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided 315 between the anode surface and the cathode surface. For example, a first high voltage electric potential may be induced between the anode surface and the cathode surface, and the first working fluid may be induced 320 to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

Referring back to FIG. 2, the second working fluid may be exposed 220 to a high-voltage electric field to generate a second plasma. As shown in FIG. 3, exposing 220 the second working fluid to the high-voltage electric field may include providing 305 an anode surface and providing 310 a cathode surface. The anode surface and the cathode surface may be separated by a distance to create a gap between the two surfaces. The distance may generally be selected such that (for the electrical voltage selected), the electrical field is about 0.3 kV/cm to about 8.0 kV/cm, including about 0.3 kV/cm, about 0.3149 kV/cm, about 0.5 kV/cm, about 0.75 kV/cm, about 1.0 kV/cm, about 1.25 kV/cm, about 1.5 kV/cm, about 1.574 kV/cm, about 2.0 kV/cm, about 2.5 kV/cm, about 3.0 kV/cm, about 3.149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided 315 between the anode surface and the cathode surface. For example, a second high voltage electric potential may be induced between the anode surface and the cathode surface, and the second working fluid may be induced 320 to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

Referring back to FIG. 2, the third working fluid may be exposed 230 to a high-voltage electric field to generate a third plasma. As shown in FIG. 3, exposing 230 the third working fluid to the high-voltage electric field may include providing 305 an anode surface and providing 310 a cathode surface. The anode surface and the cathode surface may be separated by a distance to create a gap between the two surfaces. The distance may generally be selected such that (for the electrical voltage selected), the electrical field is about 0.3 kV/cm to about 8.0 kV/cm, including about 0.3 kV/cm, about 0.3149 kV/cm, about 0.5 kV/cm, about 0.75 kV/cm, about 1.0 kV/cm, about 1.25 kV/cm, about 1.5 kV/cm, about 1.574 kV/cm, about 2.0 kV/cm, about 2.5 kV/cm, about 3.0 kV/cm, about 3.149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints). Thus, to achieve a desired electrical field, a voltage potential may be provided 315 between the anode surface and the cathode surface. For example, a third high voltage electric potential may be induced between the anode surface and the cathode surface, and the third working fluid may be induced 320 to traverse the gap between the two surfaces. In one non-limiting embodiment, the high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). Thus, for example, a voltage between the anode surface and the cathode surface (which is 0.3175 cm) is 2.4 kV, thereby resulting in an electrical field of about 7.559 kV/cm. In another non-limiting embodiment, the high-voltage electric potential may be an alternating current (AC) potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

It may be understood that the anode and cathode surfaces contacting the first working fluid, the second working fluid, and the third working fluid may be the same set of surfaces or they may be different sets of surfaces. If each working fluid contacts an independent pair of anode and cathode surfaces, the respective gap distances may be essentially the same or different, and high voltage electric potentials to which the working fluids are exposed may have essentially the same or different characteristics.

In one non-limiting example, exposing 210 the first working fluid to a first high-voltage electric field may include causing the first working fluid to pass through a first plasma torch. In another non-limiting example, exposing 220 the second working fluid to a second high-voltage electric field may include causing the second working fluid to pass through a second plasma torch. In another non-limiting example, exposing 230 the third working fluid to a third high-voltage electric field may include causing the third working fluid to pass through a third plasma torch. The first working fluid, the second working fluid, and the third working fluid may pass through the same plasma torch or may pass through individual plasma torches. In addition, the first working fluid, the second working fluid, and the third working fluid may pass through a plasma torch consecutively or may pass through a plasma torch at substantially the same time.

In some embodiments, exposing 210, 220, 230 the various working fluids to various high-voltage electric fields may cause the various plasmas to reach a temperature of about 36,000° F. (20,000° C.). The temperature may be sufficiently high to enable effective disassociation of various individual compounds in each of the various working fluids, as previously described herein.

In various embodiments, a feedstock may be provided 232. As previously described herein, the feedstock may generally include one or more of bagasse, coal, wood, green waste, sugar beets, corn, or bio-waste products. The first, second, and third plasmas may be combined 235 with the feedstock in any temporal or spatial order to form a mixture. For example, the first plasma, the second plasma, and the third plasma may be combined 235 with the feedstock by directing the second plasma to mix with the first plasma, the third plasma, and the feedstock, directing the first plasma to mix with the second plasma, the third plasma, and the feedstock, directing the third plasma to mix with the first plasma, the second plasma, and the feedstock, directing the feedstock to combine with the first plasma, the second plasma, and the third plasma, or directing the first plasma, the second plasma, the third plasma, and the feedstock to mix together. Combining 235 the various ingredients may be via any method of combining, including, but not limited to, mixing, admixing, contacting, dissolving, or the like. Combining 235 the first plasma, the second plasma, the third plasma, and the feedstock may form a mixture containing all three plasmas and the feedstock. The mixture may be a homogenous mixture or a heterogeneous mixture. In some non-limiting embodiments, the mixture may have a temperature of about 7232° F. to about 10,832° F. (about 4000° C. to about 6000° C.), including about 7232° F., about 7300° F., about 7500° F., about 8000° F., about 8500° F., about 9000° F., about 9500° F., about 10,000° F., about 10,500° F., about 10,832° F., or any value or range between any two of these values (including endpoints). Thus, the mixture may cool from the initial temperatures of the first, second, and third plasmas upon passing through the respective high-voltage electrical fields.

In some embodiments, the mixture may be transported 240 to the heat exchanger. Transporting 240 is not limited by this disclosure, and may be via any method of transport. Any number of pumps, conduit, channels, ducts, pipes, and/or the like may be used to transport 240 the mixture.

In various embodiments, the mixture may be cooled 245 to a temperature of about 100° F. to about 2950° F. (about 38° C. to about 1620° C.), including about 38° C., about 100° C., about 150° C., about 200° C., about 260° C., about 500° C., about 750° C., about 1100° C., about 1300° C., about 1600° C., about 1620° C., or any value or range between any of these values (including endpoints). In particular embodiments, the mixture may be cooled 245 to a temperature of about 100° F. to about 400° F. (about 38° C. to about 204° C.). In some embodiments, cooling may effect a change in composition of the mixture, such as dissociation of various components, as described herein. Thus, the components may be separated via a gas separator and directed to various holding containers, as described in greater detail herein.

Figure 4:
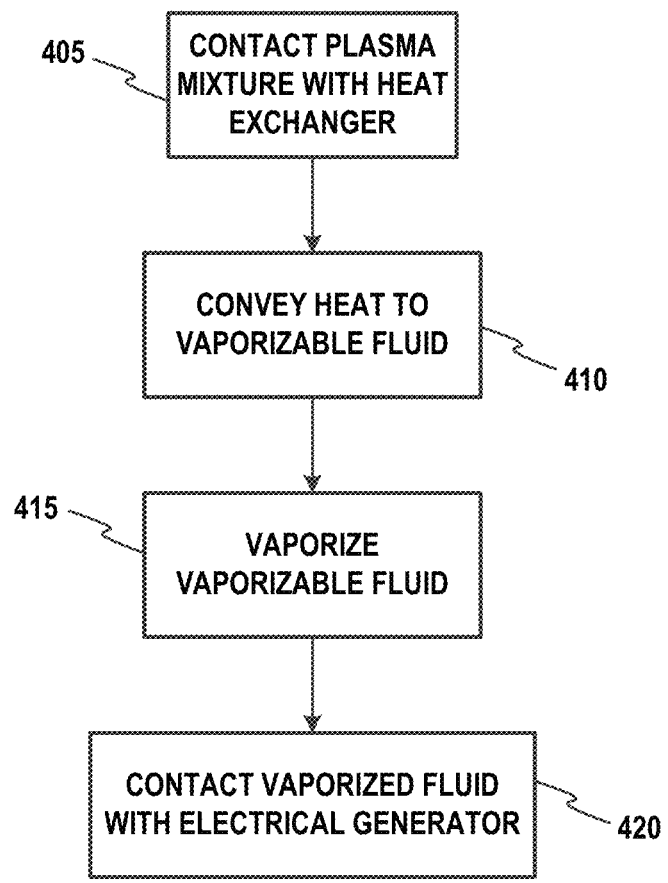
FIG. 4 depicts a flow diagram of a method of cooling a mixture according to an embodiment.

In some embodiments, as shown in FIG. 4, cooling 245 may be completed by contacting 405 the mixture with a heat exchanger within a heat exchange device, such as, for example, a HRSG, to produce a cooled mixture. In some embodiments, the heat exchanged from the mixture may be conveyed 410 by the heat exchange device to provide heat to a recovery steam generator, as described in greater detail herein. The steam generated by the heat transfer to the recovery steam generator may provide preheated water vapor that may be used at least in part as the second working fluid for conversion into a plasma. Accordingly, the steam generated by the heat transfer may increase an efficiency of the systems and methods described herein by providing a reusable heat source. In some embodiments, the recovery steam generator may use the heat from the mixture to heat and vaporize 415 a vaporizable fluid (such as liquid water or the like). The resulting vaporized fluid (e.g., the steam) may be directed to and contacted 420 with a steam-powered electrical turbine. The steam-powered electrical turbine may, in turn, generate electric power that may be used, at least in part, for providing electrical power to the system described herein and/or a facility used to generate the fuel.

In various embodiments, cooling 245 the plasma mixture may include cooling with liquid oxygen ($O_2$) to reduce the plasma mixture from a first temperature to a second temperature. The first temperature, as described herein, may be about 7232° F. to about 10,832° F. (about 4000° C. to about 6000° C.). The second temperature, as described herein, may be about 4892° F. to about 5432° F. (about 2700° C. to about 3000° C.). This cooling 245 may allow for a split of $O_2$ and $H_2O$ in the plasma mixture to become $O^-$ and $O^+$, $H^+$ and $OH^-$, and/or $H^+$ and $OH^+$. The cooling 245 may further allow for thermal chemical reconversion, thereby resulting in compounds $H_2$, $H_2O$, $O_2$, and/or $H_2O_2$.

In various embodiments, cooling 245 may result in a water-gas shift reaction (WGSR). A WGSR is a reversible chemical reaction in which carbon monoxide reacts with water vapor to form carbon dioxide and hydrogen (the mixture of carbon monoxide and hydrogen is known as water gas):

$$CO_{(g)} + H_2O_{(g)} \rightarrow CO_{2(g)} + H_{2(g)}$$

where the $\Delta H_{reac} = -41.16$ kJ at 298.15K.

The WGSR may be sensitive to temperature, with the tendency to shift towards reactants as temperature increases due to Le Chatelier's principle. Over the temperature range of about 600 K to about 2000 K, the logarithm of the equilibrium constant for the WGSR is given by $$\log_{10} K_{equil} = \frac{2408.1}{T} + 1.5350 \times \log_{10} T - 7.452 \times 10^{-5}(T) - 6.7753$$

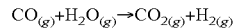

where the value of $K_{equil}$ approaches 1 at 1,100K. The process may be used in two stages. A first stage may include a high-temperature shift (HTS) at about 662° F. (350° C.). A second stage may include a low-temperature shift (LTS) at about 374° F. to about 410° F. (about 190° C. to about 210° C.). Standard industrial catalysts for this process may include iron oxide promoted with chromium oxide for the HTS step and copper on a mixed support composed of zinc oxide and aluminum oxide for the LTS step.

In various embodiments, the cooled mixture may include at least carbon monoxide and hydrogen gas. In some non-limiting embodiments, the cooled mixture may include carbon monoxide and hydrogen gas in a ratio of about 1:2 to about 1:5, including about 1:2, about 1:3, about 1:4, about 1:5, or any value or range between any two of these values (including endpoints). In various embodiments, the ratio of the mixture may be effectively measured and/or maintained by placing the mixture into a gas separator and using volumetric flow metering to add or remove components to or from the gas holding containers. Accordingly, various flow meters may be used to indicate an amount of gas that can be used to maintain a specified ratio. In some embodiments, it may be important to ensure a proper ratio of carbon monoxide to hydrogen gas for an effective Fischer-Tropsch process, to ensure the catalyst (as described herein) is not contaminated, and/or to ensure the catalyst is not degraded above a normal degradation.

Referring again to FIG. 2, in various embodiments, the cooled mixture may be contacted 250 with a catalyst. Contacting 250 the cooled mixture with a catalyst may result in forming a fuel. The type of fuel that results from contacting 250 may be determined by the ratio of hydrogen gas to carbon monoxide in the mixture, as described in greater detail herein. Contacting 250 the cooled mixture with the catalyst may include transporting the cooled mixture to the second processing chamber 130 (FIG. 1A). The catalyst may be, for example, a Fischer-Tropsch (F-T)-type catalyst or a F-T catalyst. In some embodiments, the F-T catalyst may contain iron, cobalt, nickel, or ruthenium. In addition, the F-T catalyst may be supported, promoted, and/or activated by one or more additional materials. In some embodiments, the catalyst may include at least one of cobalt, iron, ruthenium, nickel, copper, an alkali metal oxide, silica, alumina, or a zeolite. In some embodiments, the catalyst may be a Fischer-Tropsch variation catalyst, such as, for example, various catalysts that are commercially available from Emerging Fuels Technology (Tulsa, Okla.). In some embodiments, the catalyst may degrade over a period of time and may be replaced.

In various embodiments, the fuel may be collected 255. Collection is not limited by this disclosure, and may include any form of collection, storage, transport, dispensing, and/or the like. For example, in some embodiments, the fuel may be collected 255 in the fuel storage tank 135 (FIG. 1A).

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera As a non-limiting example, each range discussed herein can be readily broken down into a lower third, middle third and upper third, et cetera As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of making fuel, the method comprising:
providing a first working fluid of oxygen gas;
exposing the first working fluid to a first electric field to produce a first plasma;
providing a second working fluid of water vapor;
exposing the second working fluid to a second electric field to produce a second plasma;
providing a third working fluid of carbon dioxide;
exposing the third working fluid to a third electric field to produce a third plasma;
providing a carbon-based feedstock;
contacting the carbon-based feedstock with the third plasma, the second plasma, and the first plasma within a processing chamber to form a mixture;
cooling the mixture using a heat exchange device to form a cooled mixture; and
contacting the cooled mixture with a catalyst to form a fuel.

2. The method of claim 1, further comprising transporting the mixture to the heat exchange device.

3. The method of claim 1, further comprising collecting the fuel.

4. The method of claim 1, wherein exposing the first working fluid to the first electric field comprises:
providing an anode surface;
providing a cathode surface at a distance from the anode surface to create a gap between the anode surface and the cathode surface;
providing an electric potential between the anode surface and the cathode surface of about 2.4 kV times the distance in centimeters to about 60 kV times the distance in centimeters; and
causing the first working fluid to traverse the gap.

5. The method of claim 4, wherein the electric potential has a frequency of about 1 MHz to about 50 MHz.

6. The method of claim 1, wherein exposing the second working fluid to the second electric field comprises:
providing an anode surface;
providing a cathode surface at a distance from the anode surface to create a gap between the anode surface and the cathode surface;
providing an electric potential between the anode surface and the cathode surface of about 2.4 kV times the distance in centimeters to about 60 kV times the distance in centimeters; and
causing the second working fluid to traverse the gap.

7. The method of claim 6, wherein the electric potential has a frequency of about 1 MHz to about 50 MHz.

8. The method of claim 1, wherein exposing the third working fluid to the third electric field comprises:
providing an anode surface;
providing a cathode surface at a distance from the anode surface to create a gap between the anode surface and the cathode surface;
providing an electric potential between the anode surface and the cathode surface of about 2.4 kV times the distance in centimeters to about 60 kV times the distance in centimeters; and
causing the third working fluid to traverse the gap.

9. The method of claim 8, wherein the electric potential has a frequency of about 1 MHz to about 50 MHz.

10. The method of claim 1, wherein exposing the first working fluid to the first electric field comprises causing the first working fluid to pass through a plasma torch.

11. The method of claim 1, wherein exposing the second working fluid to the second electric field comprises causing the second working fluid to pass through a plasma torch.

12. The method of claim 1, wherein exposing the third working fluid to the third electric field comprises causing the third working fluid to pass through a plasma torch.

13. The method of claim 1, wherein the carbon-based feed stock comprises at least one of bagasse, coal, wood, green waste, sugar beets, corn, or bio-waste products.

14. The method of claim 1, wherein the mixture has a temperature of about 7232° F. (4000° C.) to about 36032° F. (20000° C.).

15. The method of claim 1, wherein cooling the mixture comprises cooling the mixture to a temperature of about 100° F. (38° C.) to about 2950° F. (1620° C.).

16. The method of claim 1, wherein the heat exchange device is a heat recovery steam generator.

17. The method of claim 16, wherein the second working fluid comprises at least in part an amount of steam generated by the heat recovery steam generator.

18. The method of claim 1, wherein the cooled mixture comprises at least carbon monoxide and hydrogen gas.

19. The method of claim 1, wherein the cooled mixture comprises at least carbon monoxide and hydrogen gas in a ratio of about 1:2.

20. The method of claim 1, wherein the cooled mixture comprises carbon dioxide.

21. The method of claim 20, wherein the third working fluid comprises at least in part an amount of carbon dioxide obtained from the cooled mixture.

22. The method of claim 1, wherein the catalyst is a Fischer-Tropsch type catalyst.

23. The method of claim 1, wherein the catalyst comprises at least one of cobalt, iron, ruthenium, nickel, copper, an alkali metal oxide, silica, alumina, or a zeolite.

24. The method of claim 1, wherein the fuel comprises at least one of naphtha, diesel fuel, a diesel fuel blend, JP-8 fuel, jet fuel, a jet fuel blend, or gasoline.

25. The method of claim 1, wherein cooling the mixture using the heat exchange device comprises:
contacting the mixture with the heat exchange device, thereby conveying at least some heat from the mixture to a source of a vaporizable fluid;
vaporizing the vaporizable fluid with the at least some heat from the mixture;
contacting the vaporized fluid with an electrical generator; and
generating electrical power by the electrical generator.

* * * * *